US00PP35413P2

(12) United States Plant Patent
Smith

(10) Patent No.: US PP35,413 P2
(45) Date of Patent: Oct. 3, 2023

(54) ***CHRYSANTHEMUM* PLANT NAMED 'CIFZ0089'**

(50) Latin Name: ***Chrysanthemum* x *morifolium***
Varietal Denomination: CIFZ0089

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/233,737

(22) Filed: Apr. 19, 2021

(51) Int. Cl.
*A01H 5/02* (2018.01)
*A01H 6/14* (2018.01)

(52) U.S. Cl.
USPC ..... Plt./289

(58) Field of Classification Search
USPC ..... Plt./287, 289, 290
CPC ... A01H 5/02; A01H 5/00; A01H 6/14; A01H 6/1424
See application file for complete search history.

(56) References Cited

U.S. PATENT DOCUMENTS

PP16,383 P2 * 3/2006 Smith ..... A01H 5/02 Plt./289

* cited by examiner

*Primary Examiner* — June Hwu
(74) *Attorney, Agent, or Firm* — Dale Skalla

(57) ABSTRACT

A new garden type *Chrysanthemum* plant named 'CIFZ0089' particularly distinguished by its medium size plant with mound plant habit, a small size decorative flower, yellow flower color and a natural season response late September.

1 Drawing Sheet

Latin name of the genus and species of the plant claimed: *Chrysanthemum* x *morifolium*.

Varietal denomination: 'CIFZ0089'.

BACKGROUND OF THE NEW PLANT

The present invention comprises a new *Chrysanthemum*, botanically known as *Chrysanthemum* x *morifolium*, and hereinafter referred to by the variety name 'CIFZ0089'.

'CIFZ0089' is a product of a planned breeding program. The new cultivar has a medium size plant with mound plant habit, a small size decorative flower, yellow flower color and a natural season response late September.

'CIFZ0089' originated from a mutation of X-ray treated cuttings in August 2018 in Gilroy, Calif. 'CIFZ0089' was selected from the resulting plants on Jan. 11, 2019 in Gilroy, Calif.

The female parent was the variety 'CIFZ0070', U.S. Plant Pat. No. 31,323.

TABLE 1

Characteristics of the female parent, compared to 'CIFZ0089':

| Trait | 'CIFZ0089' | 'CIFZ0070', U.S. Plant Pat. No. 31,323 |
|---|---|---|
| Natural response: | ½ to 1 week faster | ½ to 1 week slower |
| Blackcloth response: | Similar | Similar |
| Flower size: | Similar | Similar |
| Flower color: | More yellow/less orange | More orange/less yellow |
| Flower type: | Similar | Similar |
| Plant size: | Smaller | Larger |
| Plant habit: | Similar | Similar |
| Plant strength: | Stronger | Weaker |

As the new variety is the result of mutation breeding, there is no male parent.

The first act of asexual reproduction of 'Breeder reference' was accomplished when vegetative stem cuttings were propagated from the initial selection in March 2019 in Gilroy, Calif.

BRIEF SUMMARY OF INVENTION

Horticultural examination of plants grown from cuttings of the plant initiated in March 2019 and continuing thereafter, has demonstrated that the combination of characteristics as herein disclosed for 'CIFZ0089' are firmly fixed and are retained through successive generations of asexual reproduction.

'CIFZ0089' has not been observed under all possible environmental conditions. The phenotype may vary significantly with variations in environment such as temperature, light intensity and day length.

A Plant Breeder's Right for this cultivar has not yet been applied for. 'CIFZ0089' has not been made publicly available prior to the effective filing date of this application, notwithstanding any disclosure that may have been made less than one year prior to the effective filing date of this application by the inventor or another who obtained 'CIFZ0089' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0089' with colors being as true as possible with an illustration of this type.

Figure 1:
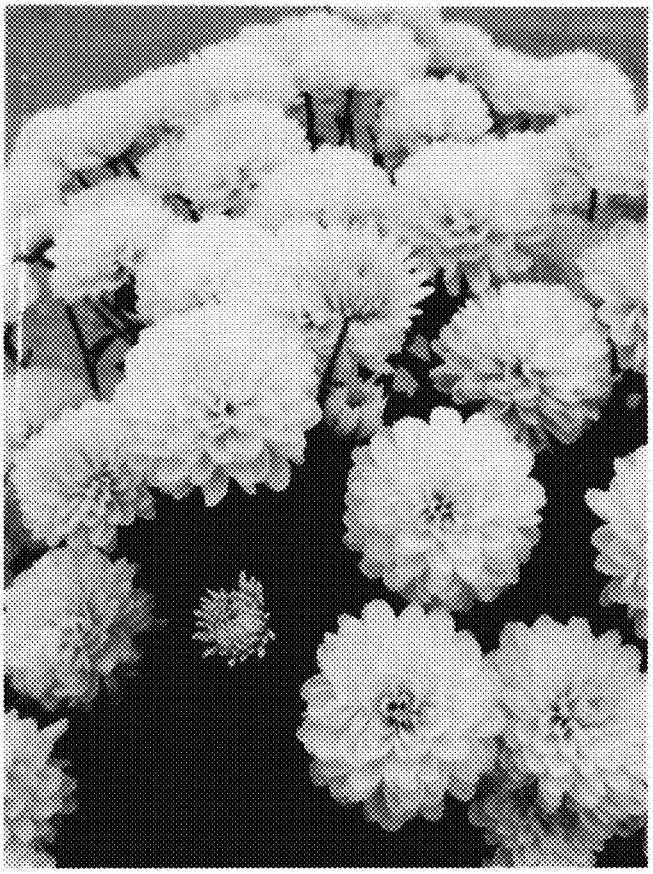
Figure 2:
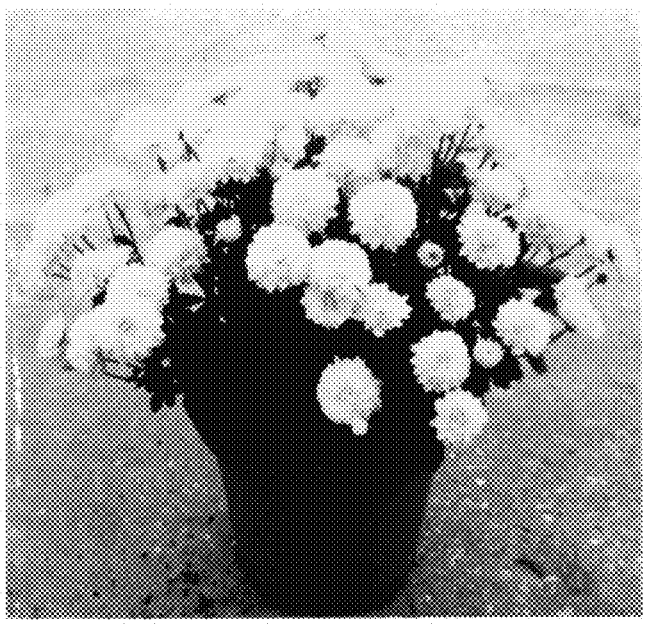

The photographic drawing shows in FIG. 1 a close view of flower of the new variety and in FIG. 2 a flowering plant from an indoor trial.

The aforementioned photographs: FIG. 1, as well as FIG. 2 were taken in March 2021 both showing a plant from the same blackcloth indoor trial in Enkhuizen, The Netherlands.

These plants were about 10 weeks of age. One rooted cutting per pot had been planted in a one gallon pot, not pinched in week 53, 2020 and black clothed from week 3. Plants started flowering mid March 2021.

DETAILED BOTANICAL DESCRIPTION

The measurements were taken in Enkhuizen, The Netherlands in March 2021 on the plants from an indoor blackcloth trial.

Color references are made to The Royal Horticultural Society Colour Chart (R.H.S.) 2015.

TABLE 2

DIFFERENCES BETWEEN THE NEW VARIETY 'CIFZ0089' AND TWO MOST SIMILAR VARIETIES:

| Trait | 'CIFZ0089' | 'Golden Yocheryl', U.S. Plant Pat. No. 16,383 |
|---|---|---|
| Natural response: | 1 week faster | 1 week slower |
| Blackcloth response: | Similar | Similar |
| Flower size: | Smaller | Larger |
| Flower type: | Similar | Similar |
| Plant size: | Taller in blackcloth, smaller overall natural | Shorter in blackcloth, larger overall in natural |
| Plant habit: | Similar | Similar |
| Flower longevity: | Similar | Similar |
| Plant strength: | Weaker | Stronger |

TABLE 3

| Trait | 'CIFZ0089' | 'Conaco Yellow', Unpatented |
|---|---|---|
| Natural response: | Similar | Similar |
| Blackcloth response: | 1 week faster | 1 week slower |
| Flower size: | Smaller | Larger |
| Flower type: | Similar | Similar |
| Plant size: | Larger | Smaller |
| Plant habit: | More upright in blackcloth | More mounded in blackcloth |
| Flower longevity: | 25% longer | 25% shorter |
| Plant strength: | Weaker | Stronger |

Plant:

*Form, growth and habit.*—Herbaceous garden-type, stems. Upright and outwardly spreading, freely branching, strong and moderately vigorous growth habit.

*Plant height (above soil).*—17-19 cm.

*Plant height (inflorescence included).*—20-23 cm.

*Plant width.*—28-30 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 139A.

*Immature leaf, color lower surface.*—RHS 139B.

*Mature leaf, color, upper surface.*—RHS NN137A.

*Mature leaf, color lower surface.*—RHS NN137B.

*Length.*—3.2 cm.

*Width.*—3.0 cm.

*Shape.*1'Ovate, with distinct lobes.

*Base shape.*—Attenuate.

*Apex shape.*—Mucronate.

*Margin.*—5-lobed (palmate), edge dentate.

*Number of margin indentations.*—Medium.

*Depth of margin indentations.*—Medium.

*Leaf length terminal lobe relative to total leaf length.*—Medium.

*Leaf depth lower lateral sinus.*—Medium.

*Texture, upper surface.*—Bifid hairs.

*Texture, lower surface.*—Bifid hairs.

*Color of veins, upper surface.*—RHS 138B.

*Color of veins, lower surface.*—RHS 138A.

*Pattern of veining.*—Palmate.

*Petiole color.*—RHS 139A.

*Petiole length.*—1.0-1.1 cm.

*Diameter.*—0.2-0.3 cm.

*Texture.*—Bifid hairs.

*Presence of stipules.*—Yes.

*If present, size of stipules.*—Small.

Stem:

*Quantity of main branches per plant.*—6-8.

*Color of stem.*—RHS 138A.

*Length of stem.*—8.0-9.0 cm.

*Diameter.*—0.5 cm.

*Length of internodes.*—2.5-3.0 cm.

*Texture.*—Bifid hairs.

*Color of peduncle.*—RHS 138A.

*Length of peduncle.*—4.0-4.5 cm.

*Peduncle diameter.*—0.3 cm.

*Texture.*—Bifid hairs.

Inflorescence:

*Type.*—Compositae, solitary, decorative-type inflorescences borne terminally above foliage, ligulate ray florets arranged acropetally on a capitulum giving a double flower.

*Quantity of short days to flowering (response time).*—Approximately 7 weeks.

*Quantity of inflorescences per plant.*—80-90 with some buds developing.

*Lastingness of individual blooms on the plant.*—About six weeks from first color.

*Fragrance.*—Slightly spicy.

Bud (when showing color):

*Color.*—RHS 8A with center of bud RHS 139C.

*Length.*—0.8-0.9 cm.

*Width.*—1.0-1.1 cm.

*Shape.*—Oblate.

Immature inflorescence:

*Diameter.*—2.0-2.5 cm.

*Color of ray florets, outer ray florets, upper surface.*—RHS 9A; inner whorls RHS 13A and up to 10 yellow-greenish petals in the center of the flower; RHS N144A.

*Color of ray florets, inner ray florets, upper surface.*—RHS N144A.

*Color of ray florets, outer whorls, lower surface.*—RHS 9A.

*Color of ray florets, inner whorls, lower surface.*—RHS N144A.

Mature inflorescence:
*Diameter.*—4.6 cm.
*Depth.*—1.4 cm.
*Total diameter of disc.*—No disc present.
*Receptacle color.*—RHS 143C.
*Receptacle height.*—0.6 cm.
*Receptacle diameter.*—1.6 cm.
*Length of corolla tube.*—Medium.

Ray florets:
*Average quantity of florets.*—140-150 in several whorls.
*Average number of rows or whorls of ray florets.*—About 16.
*Density of ray florets.*—Dense.
*Predominant type of ray floret.*—Ligulate.
*Color of ray florets, outer ray florets, upper surface.*—RHS 9A.
*Color of ray florets, inner ray florets, upper surface.*—RHS 13A.
*Color of ray florets, outer whorls, lower surface.*—RHS 9A.
*Color of ray florets, inner whorls, lower surface.*—RHS 13A.
*Ray floret longitudinal axis curvature strength of the inner and outer rows.*—Curvature for the outer rows is weak and inner rows is weak to medium.
*Ray floret corolla tube shape.*—Flattened.
*Length.*—2.7 cm.
*Width/diameter.*—0.5-0.6 cm.
*Shape.*—Elliptical.
*Apex shape.*—Mostly obtuse and dentate.
*Base shape.*—Tube.
*Margin: entire.*—Small incisions may be present at tip.
*Margin: type of rolling.*—Moderately involute.
*Texture, upper surface.*—Papillate.
*Lower surface.*—Papillate.
*Ribs present.*—Yes.
*Number of keels.*—2.
*Profile at widest point.*—Moderately concave.
*Longitudinal axis shape.*—Straight, occasionally twisted.

Disc florets:
*Number of disc florets.*—0.

Inflorescence (at moment of senescence):
*Color of ray florets, upper surface.*—RHS 12A.
*Color of ray florets, lower surface.*—RHS 12B.

Phyllaries:
*Quantity.*—20-25.
*Color, upper surface.*—RHS 143C.
*Color, lower surface.*—RHS 143A.
*Length.*—0.6 cm.
*Width.*—0.1-0.2 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.

Reproductive organs:
*Pistil.*—One.
*Length.*—0.4 cm.
*Style color.*—RHS 150C.
*Style length.*—0.3 cm.
*Stigma color.*—RHS 7D.
*Stigma shape.*—Bi-parted.
*Ovary color.*—RHS 145C.
*Ovary length.*—0.2 cm.
*Ovary width.*—0.1 cm.

Androecium: As no disc florets are present, no androecium developed.
*Fertility/seed set.*—Has not been determined to date.
*Disease/pest resistance.*—Has not been determined to date.
*Hardiness.*—Has not been determined to date.

What is claimed is:

1. A new and distinct variety of *Chrysanthemum* plant named 'CIFZ0089' substantially as illustrated and described herein.

* * * * *